United States Patent [19]

Bienhaus et al.

[11] Patent Number: 5,746,978
[45] Date of Patent: May 5, 1998

[54] DEVICE FOR TREATING NUCLEIC ACIDS FROM A SAMPLE

[75] Inventors: Gerhard Bienhaus, Wielenbach; Hans Lange, Lampertheim, both of Germany

[73] Assignee: Boehringer Mannheim GmbH, Mannheim, Germany

[21] Appl. No.: 895,920

[22] Filed: Jul. 17, 1997

Related U.S. Application Data

[63] Continuation of Ser. No. 490,987, Jun. 15, 1995, abandoned.

[30] Foreign Application Priority Data

Jun. 15, 1994 [DE] Germany .................. 44 20 732.8

[51] Int. Cl.$^6$ .............. G01N 15/06; C12Q 1/68; C12P 19/34; C07H 21/04
[52] U.S. Cl. ................ 422/68.1; 435/6; 435/5; 435/91.1; 435/91.2; 435/814; 435/815; 210/175; 210/143; 210/294; 210/222; 210/695; 210/500.1; 536/24.3; 536/24.32; 536/24.33
[58] Field of Search ............... 435/6, 5, 91.2, 435/814, 815; 422/68.1; 536/25.3; 417/243; 209/11; 210/222, 500.1, 143, 175, 294; 423/210; 55/220

[56] References Cited

U.S. PATENT DOCUMENTS

| | | | |
|---|---|---|---|
| 5,176,203 | 1/1993 | Larzul | 165/61 |
| 5,229,297 | 7/1993 | Schnipelsky . | |
| 5,288,463 | 2/1994 | Chemelli | 422/58 |
| 5,415,839 | 5/1995 | Zaun et al. | 422/64 |
| 5,422,271 | 6/1995 | Chen et al. | 435/287 |
| 5,451,500 | 9/1995 | Stapleton | 435/6 |
| 5,460,780 | 10/1995 | Devaney, Jr. et al. | 422/99 |

FOREIGN PATENT DOCUMENTS

| | | |
|---|---|---|
| 0 245 945 | 11/1987 | European Pat. Off. . |
| 0 325 763 | 12/1988 | European Pat. Off. . |
| 0 381 501 | 2/1990 | European Pat. Off. . |
| 0 245 945 | 11/1993 | European Pat. Off. . |
| 0 570 867 | 11/1993 | European Pat. Off. . |
| 2672301 | 8/1992 | France . |
| WO 87/07954 | 12/1987 | WIPO . |
| WO 90/02821 | 3/1990 | WIPO . |
| WO93/13220 | 7/1993 | WIPO . |
| WO93/22020 | 11/1993 | WIPO . |
| WO93/22058 | 11/1993 | WIPO . |
| WO 94/04929 | 3/1994 | WIPO . |
| WO 94/26414 | 11/1994 | WIPO . |
| WO94/25785 | 11/1994 | WIPO . |

OTHER PUBLICATIONS

Blumberg, Methods in Enzymology, A Guide to Molecular Cloning Techniques, vol. 152, p. 17, 1987.
Lizardi et al. Rapid Isolation of RNA using Proteinase K and Sodium Perchlorate Analytical Biochemistry 98: 116–122, 1979.
Wilber et al. Diagnostic Molecular Microbiology, Reverse Transcriptase PCR for Hepatitis C Virus RNA, vol. 2.4, pp. 191–252, 1993.
Eisenach et al. Bacterial Pathogens, "PCR Detection of Mycobacterium" in PCR Technology, Principles and Applications for DNA Amplification, Eds. Erlich et al., Stockton PRess, pp. 191–252, 1993.
Boom et al., J. of Clinical Microbiology, "Rapid and Simple Method for Purification of Nucleic Acids", vol. 28, No. 3., pp. 95–503, 1990.
Lewin et al. "Cell Isolation Techniques: Use of Enzymes and Chelators," Methods in Enzymology, vol. 171: 444–589, 1989.
"PCR Carry–Over", *BFE*, by Martin Heinrich, vol. 8, No. 10, Oct. 1991, pp. 594–596.

*Primary Examiner*—W. Gary Jones
*Assistant Examiner*—Dianne Rees
*Attorney, Agent, or Firm*—Nikaido, Marmelstein, Murray & Oram LLP

[57] ABSTRACT

Device for the treatment of nucleic acids from the sample, comprising a first reaction chamber for separating the nucleic acids from other sample components, and a second reaction chamber for the amplification of the nucleic acids, connected to said first reaction chamber via a controllable transport path.

42 Claims, 4 Drawing Sheets

DEVICE FOR TREATING NUCLEIC ACIDS FROM A SAMPLE

This application is a continuation of application Ser. No 08/490,987 filed Jun. 15, 1994 now abondoned.

Subject matter of the invention is a device for treating nucleic acids from a sample and a system for handling this device.

As compared to clinical chemistry and immunology, sample preparation plays a critical role in the analysis of nucleic acids. It is a particularly important step when amplification procedures such as the polymerase chain reaction (Mullis, U.S. Pat. No. 4,683,195) or amplification procedures based on transcription reactions are part of the analysis. A method for the analysis of nucleic acids can theoretically be split up in three partial steps; namely sample preparation where the nucleic acids from a sample are made accessible and separated from interfering sample components; then the amplification step where the amount of nucleic acids is increased; and a detection step where the nucleic acids which have formed are detected.

Currently available tests for the analysis of nucleic acids, e.g. for the detection of HIV from blood, require a whole series of chemical and physical procedural steps. They include centrifugation, decanting, and extraction. All these steps are carried out in reagent tubes. The results of the sample preparation are precipitated nucleic acids which are then again dissolved for further treatment in the amplification reaction.

EP-A-0 389 063 describes a special variant where the nucleic acids, after sample preparation, are bound to a gel. Again, this procedure comprises several centrifugation steps to separate the gel particles from the sample liquid.

A particular problem when analyzing samples for nucleic acids is the risk of contamination from outside via air, or by foreign nucleic acids carried over by the devices used for this treatment. In addition, the above listed methods are also particularly susceptible to contamination as the sample containers must be repeatedly opened and closed.

EP-B-0 381 501 describes a device for the amplification of nucleic acids and detection of the amplification products where a sample specimen is pipetted into the reaction chamber for amplification. When the amplification is completed, the liquid is transferred into a detection chamber while contact with the environment is excluded. While this device may be suitable to avoid contamination during amplification and detection, EP-B-0 381 501 completely disregards the fact that in the practice, nucleic acids must be subject to preparatory steps since they can usually not be directly used in a PCR.

It was, hence, an object of the present invention to avoid the drawbacks of prior art and to provide in particular a device for the contamination-free and simple treatment of nucleic acids.

Subject matter of the invention is, hence, a device for the treatment of nucleic acids from a sample which is characterized in that it comprises a first reaction chamber for separating nucleic acids from other sample constituents, and a second reaction chamber for the amplification of nucleic acids connected to said first chamber via a controllable path of transportation. Another subject matter of the invention is a system for the treatment of nucleic acids which is adapted to the device in accordance with the invention.

The basic idea underlying the invention is to link the steps of sample preparation and nucleic acid amplification in a particularly advantageous manner to be carried out in one single device. Such a link of steps has not yet been described to date.

Nucleic acids as understood in the invention include any type of nucleic acids, both DNA and RNA, single-stranded, double-stranded, or multiple-stranded. These nucleic acids may be contained in any type of sample, in particular liquid samples. The term sample is meant to be understood a mixture of substances. Prior to their use in the device of the invention, they may be subject to a treatment or may also be directly used in their natural status, e.g. in the form of body fluids such as blood or urine.

There exist different kinds of methods which require a treatment of nucleic acids. They include methods for the detection of nucleic acids in a sample as they are necessary for the detection of infections by nucleic acid-containing organisms. Several treatment steps are, however, also feasible in methods for the determination of the genetic status of organisms. All these methods require a series of treatment steps. As the nucleic acids only make up a very small part of the components of a mixture, it is often necessary to separate the nucleic acids from other sample components. The desired degree of separation or purification depends on the intended use of the entire treatment.

The amplification of nucleic acids is also a commonly known step in the treatment of nucleic acids. There exist several variants of methods for the amplification of nucleic acids, such as the polymerase chain reaction. The amplification of nucleic acids essentially refers to in-vitro amplification. An in-vivo amplification is, however, principally also conceivable.

Subject matter of the invention is now to link both treatment steps in one single device. In this procedure, the nucleic acids are separated from other sample components in a first reaction chamber and the nucleic acids are amplified in a second reaction chamber. In accordance with the invention, both reaction chambers are connected via a common transportation path which is configured such that the liquid is transported from first to the second reaction chamber in a given period of time.

The treatment step for separating the nucleic acids in a first reaction chamber is a complex procedure which may be further divided into the following steps depending on the type of sample used. These substeps may be carried out in more than one reaction chamber connected to one another in accordance with the invention. Said treatment step may comprise the following substeps.

a) Liquefying a solid or viscous sample.

b) Separating nucleic acid-containing compartments, such as cells or cell compartments via suitable, mostly known procedures.

c) Amplifying nucleic acid-containing compartments such as cells or cell compartments via suitable methods (e.g. according to EP-A-0260280).

d) Releasing the nucleic acids from the above-mentioned compartments.

e) Separating nucleic acids from other sample components, especially from those that have an inhibitory effect in the various amplification processes, e.g. polymerase inhibitors.

In accordance with the invention, none of these treatment steps in the first reaction chamber includes centrifugation. Possible methods are described in prior art and include enzymatic degradation reactions, various immunochemical methods with different solid phase systems such as immunoadsorption or the use of coated magnetic particles. Possible methods for separating nucleic acids include the retaining of nucleic acids in a filter material, (non-specific) immobilization of nucleic acids to an adsorbent such as silica gel or glass particles contained in a reaction chamber, or the biospecific immobilization of nucleic acids to biospecific adsorbents, e.g. affinity materials. In this case, the property of nucleic acids to form hybrids to essentially complementary nucleic acids at a solid phase may be utilized.

The nucleic acids may also be separated via chromatographic procedures in a first reaction chamber. Apart from the separation of nucleic acids, additional treatment steps for nucleic acids, e.g. filtration of nucleic acid-containing cells, lysis of these cells or labeling of nucleic acids, may also be carried out in the first reaction chamber. In accordance with the invention, it is possible to perform in the first reaction chamber in one step the lysis and immobilization of nucleic acids according to EP-A-0 389 063. Depending on the treatment to be carried out in a first reaction chamber, a heating element may also be provided adjacent to the reaction chamber. This is particularly feasible in the lysis of cells.

In all the methods described above, the risk of contamination and the risk of obtaining false-positive results is rather high prior to the amplification of the nucleic acids. Also, the processes described for sample preparation are quite diverse. An important subject matter of the invention is, therefore, the use of inexpensive, modular, disposable plastic articles which can be used in multistep processes in an essentially closed system. The device, hence, presents itself as an essentially closed system with several openings to allow the addition of reagents into at least one reaction chamber without the risk of contamination. In a first aspect of the invention, the device is a multiple reaction vessel to be used for numerous applications and uses.

The separation of the nucleic acids from other sample components is terminated when the liquid with other sample components is removed from the first reaction chamber while the amplified nucleic acids remain in said reaction chamber. To accomplish this, the first reaction chamber has not only an opening for the intake of samples into the first reaction chamber, but also an additional opening, preferably at the lower part or the bottom of the reaction chamber, which is hereinafter referred to as a valve opening. In a preferred manner, this valve opening can be closed. As soon as the sample is available in the first reaction chamber, said opening is normally closed. In order to separate other sample components from the nucleic acids, the valve opening is open as long as required and the other sample components are removed.

A closure as understood in the invention is in particular a valve closure which can be opened by applying a vacuum from the outside to the first reaction chamber. By applying a pressure that is lower with respect to the pressure in the first reaction chamber, the sample components are removed from the first reaction chamber. If these components are not subject to any further treatment, they are discarded, preferably transported into a waste container.

Since the opening for filling the reaction chamber, which is preferably in the upper part of the reaction chamber, must be closed with a suitable automatically operating lid due to the high risk of contamination, it is necessary to provide a corresponding pressure compensation. Solutions in accordance with the invention are described hereinafter.

Subsequently, the nucleic acids which have been prepared, are separated, for example, from other sample components and transferred into a second reaction chamber where they are amplified. Between the first and the second reaction chambers, it is also possible to have additional reaction chambers for further purification or other treatment steps. The nucleic acids are removed from the first reaction chamber by dissolving in a solution. Depending on the type of immobilization of the nucleic acids, this can be achieved by applying a reagent gradient, by means of a substance causing desorption, or by means of displacement. Suitable processes are known in particular from EP-A-0 389 063.

The liquid containing the nucleic acids are transported to the second reaction chamber via a transport path. In accordance with the invention, it is preferred that this transport path be controllable. Controllable means that the transport path contains means to ensure that the nucleic acid-containing solution is conveyed into the second reaction chamber and not the liquid containing the other sample components. This can be implemented, for example, by means of a conventional three-way cock where the first and the second path lead to the first and second reaction chamber, respectively, and a third path is a discarding path. When the liquid with the other sample components is to be transported across the transport path, the distribution element links the path coming from the first reaction chamber to the waste path. When the nucleic acid-containing solution is to be transferred into the second reaction chamber, the distribution element is switched such that the path from the first reaction chamber is connected to the path to the second reaction chamber. Additional possibilities of dividing the liquid flows are known. The distribution element is preferably controlled via a central control unit, so that the addition of reagent into the first reaction chamber, the initiation of transportation of liquid with the other sample components or the nucleic acid-containing solution and the positioning of the distribution element can be coordinated.

The second reaction chamber used for the amplification reaction contains the necessary reagents either prior to adding the nucleic acid solution, or these reagents are added to the nucleic acid-containing solution in the second reaction chamber via an opening. In a preferred manner, the opening for reducing the risk of contamination can be closed from the outside and is closed immediately after all amplification conditions have been adjusted. If the addition of further reagent is necessary at a later time, this opening can be re-opened. Another common possibility of amplifying nucleic acids is PCR, e.g. according to EP-A-0 200 362. When this possibility is applied, the second reaction chamber is preferably configured such that all temperature changes can be completed therein rapidly.

After the amplification reaction, the reaction mixture can remain in the second reaction chamber to carry out further reactions or it can be removed therefrom. This can be done either via the above-mentioned closable opening or provision may be made for a second opening, as done for the first reaction chamber.

For the nucleic acid detection test, the detection can be carried out in the second reaction chamber as described, for example in DE-A-43 44 742, or after transfer into an additional vessel, for example a third reaction chamber.

The individual elements of the device in accordance with the invention are principally known or are easy to manufacture. They include, for example, tubes where the bottom is provided with a valve that can be opened by applying a low pressure. In this case, a rubber sealing lip provided with slots at its center expands into direction of the low pressure and the outer outlet openings of the tube bottom are exposed. If the low pressure is terminated, the rubber sealing lip springs back into its initial position and seals the outlet openings.

The tube can be made of suitable materials such as plastic or of glass. The rubber sealing lip can be made of an elastic caoutchouc rubber or a comparable elastic material. The material must be one of a high elasticity to allow opening by applying a minor low pressure and vice-versa.

Manufacture can be accomplished in two steps: a) processing the plastic by means of injection molding to provide the base with the corresponding shape with a projection at its lower end. b) inserting a rubber sealing lip providing its edge with a crimp in a melting process thus attaching the rubber sealing lip to the base.

The controllable transport path can be a tubular element, but may also be a rigid plastic pipe. The distribution elements can be conventional three-way distribution elements. The second reaction chamber can practically be any tube known from reagent analyzers. In a particularly advantageous manner, the device of the invention is formed in one single piece, except the movable parts such as valve or distribution element. This can be accomplished in an injection-molding procedure.

An advantage of the device in accordance with the invention is that it can be configured as a disposable device, i.e. after separation of the nucleic acids and their amplification, and after retrieving the amplified nucleic acids, the device can be discarded.

Another possible embodiment of the device of the invention proposes that the device consists of individual modules which can be combined in any desired way depending on the type of treatment to be carried out, the type of sample used and the type of treatment desired. A module as used in the invention is meant to be a device provided for a treatment step, which can be connected and combined with other devices to process a series of treatment steps in a simple manner. In one aspect of the invention, the device essentially consists of snap-on modules having an identical design which then allow a multi-step reaction. Identical design in this connection essentially means that a minimum of two modules have a similar outer shape and feature the same principle for opening the closure to seal the outlet opening. With respect to the contents of a reaction chamber of the module, there may be considerable differences depending on the use of the module. One module may, for example, contain a filter fleece, another one reagents for the lysis of cells, yet another one materials for immobilizing cells or nucleic acids. The term sanp-on modules in this respect means that the outlet of one module can be attached to the inlet of another module in a rapid and liquid-tight manner. Modules are those which have a reaction chamber and a liquid-tight closure which can be opened by applying a vacuum from the outside to the closure. In order to separate nucleic acids, the module contains all materials and reagents necessary for this separation, and also contains the specific reagents that are necessary to carry out the amplification reactions. The reaction modules can be linked to each other via distribution modules. Distribution modules contain elements for connection to the reaction modules and a waste container, the transport paths and the distribution element.

Transportation of gases and especially liquids within the device is ensured either via capillary forces or low pressure/ vacuum. The use of a low pressure is preferred. To accomplish this, a slight low pressure is applied to the waste container and/or the second reaction chamber.

Figure 1:
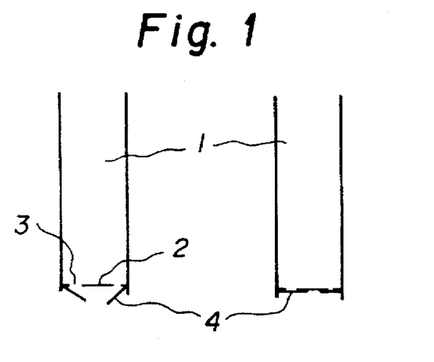

FIG. 1 shows modules that can be used for the manufacture of a device in accordance with the invention. The figure shows a universal module (1) for reaction chambers with a bottom opening that can be closed, said opening being shown in its closed and open condition. In a preferred embodiment, the universal module has a bottom (2) with several outlet openings (3) and a slotted rubber sealing lip (4).

Figure 1A:
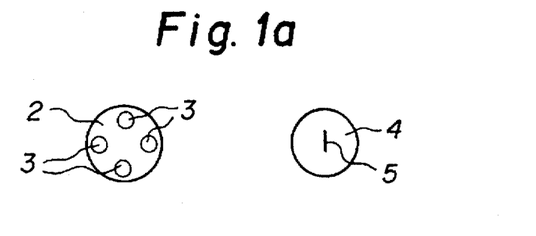

FIG. 1a is a top view of bottom (2) with outlet openings (3) and rubber sealing lip (4) with slot (5). When a low pressure is applied, rubber sealing lip (4) expands thus opening slot (5) and releasing outlet openings (3).

Figure 1B:
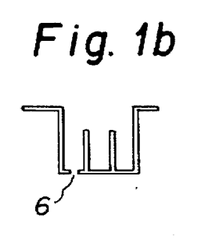
Figure 1C:
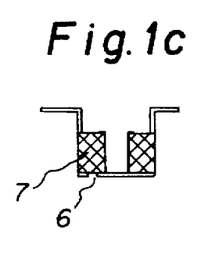
Figure 1D:
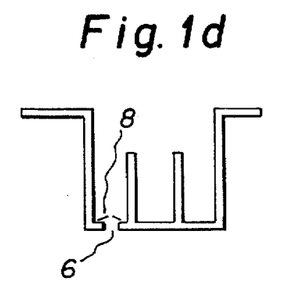

FIG. 1b is a section taken through the lid for the top opening with an aeration bore (6). The embodiments shown in FIGS. 1c and 1d are provided with a contamination protection, with a paper fleece disk (7) shown in FIG. 1c and a slotted rubber sealing lip (8) shown in FIG. 1d.

Figure 1E:
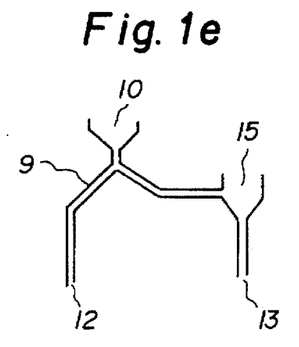

FIG. 1e is a distribution element (9) with a projection (10) for a first reaction chamber (11), a projection (12) for a waste container and a projection (13) for a second module with a second reaction chamber (14) in a serial arrangement. Opening (15) serves to add reagents and hold a lid (19).

Figure 1F:
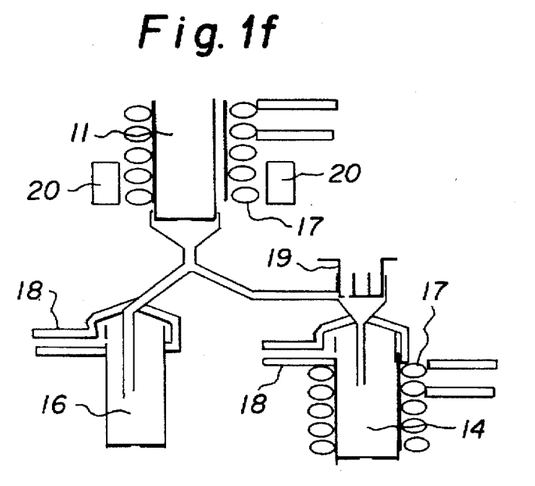

FIG. 1f shows a device in accordance with the invention having a first reaction chamber (11) and a second reaction chamber (14), a waste container (16), heating elements (17) for the first and second reaction chamber, and the connecting pieces (18) for the generation of a vacuum for a second reaction chamber and the waste container. In the position as shown, a lid (19) is provided on the distribution element in the vicinity of the second reaction chamber. The slot can be used to allow the addition of reagents for the amplification of the nucleic acids to the second reaction chamber. Further, a magnet (20) is indicated which can be used to separate magnetic particles (e.g. particles from non-magnetic phases) during or after the amplification reaction, e.g. for a preceding cell amplification by means of immunoadsorption.

Figure 1G:
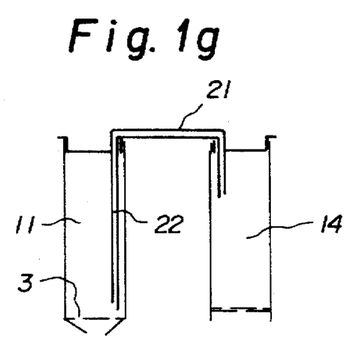

Another embodiment in a planar arrangement is shown in FIG. 1g. In this figure, the distribution element (21) is integrated in the lid solution. Capillaries (22) serve to transfer the reaction solution from the first reaction chamber (11) into the second chamber (14) by generating a low pressure in the second reaction chamber (14) when the valve in the first reaction chamber (11) is closed. Any waste which may be generated in the various reactions can be discarded directly via the bottom opening (3). It is also possible to include heating elements and magnetic separators as shown for FIG. 1f.

Figure 2:
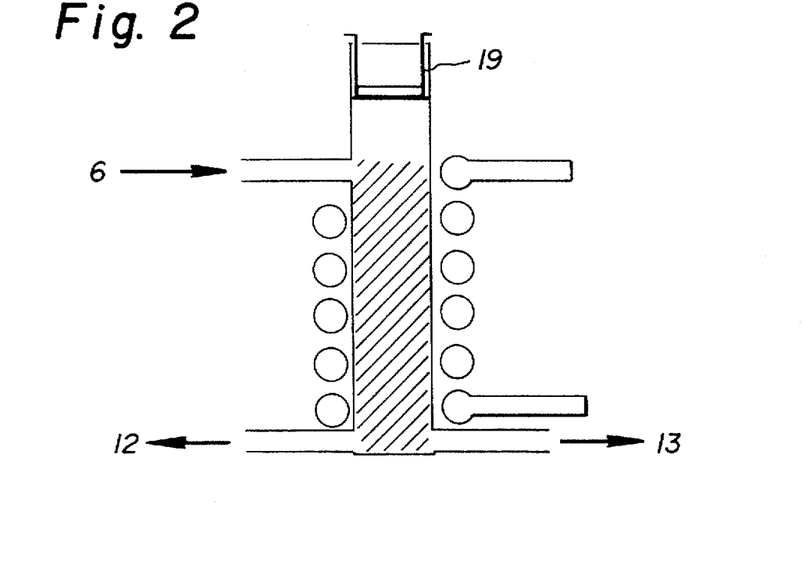

FIG. 2 is another example for the variable design of a contamination-free reaction chamber consisting of standard modules to be used for the immunological adsorption of cells. In the example shown, a lid (19) seals the module. When a vacuum is applied to outlets (12, 13), transportation of liquid from the module would be quickly terminated if there were no additional opening (6) to compensate the pressure.

Figure 3:
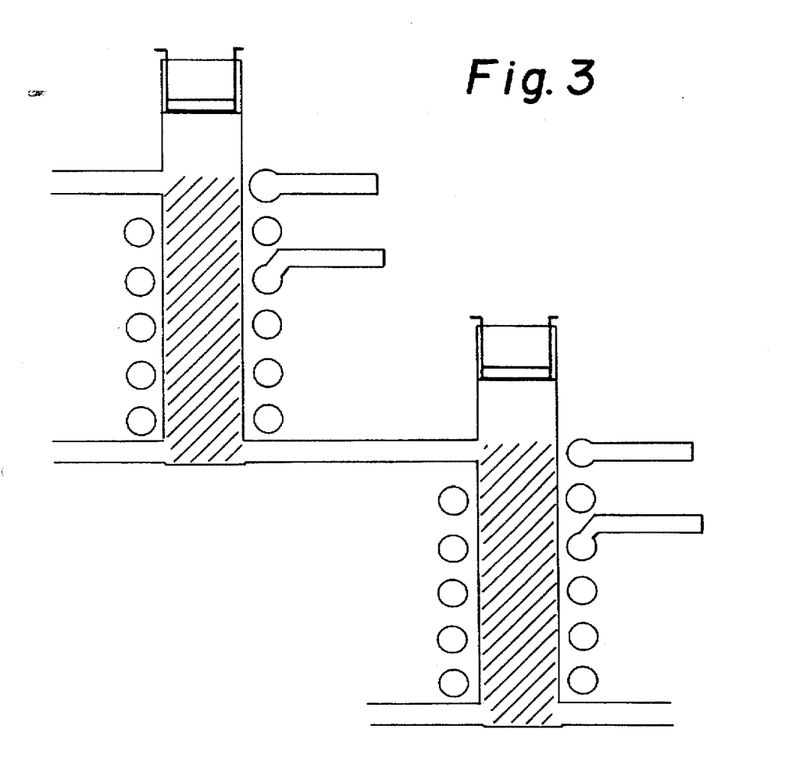

FIG. 3 is a diagrammatic representation of a combination of a module with reagents for immunoadsorption and a module for carrying out an amplification reaction of nucleic acids. It is obvious that, provided the connections are matching, the module in accordance with the invention can be adapted to each treatment step, and be provided with corresponding heating elements and magnetic separators to give a universal system consisting of simple basic modules as shown in FIG. 1a–g.

Figure 4:
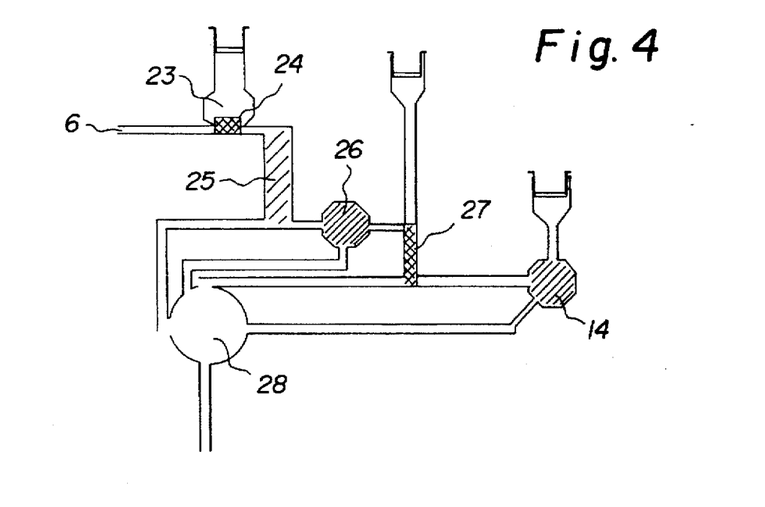

FIG. 4 shows a device, in accordance with the invention for sample preparation and amplification of nucleic acids from whole blood. Hemolysis is carried out in a reaction module (23). The desired cells are separated from remaining tissue through a coarse filter (24). The cells are applied to an immunoadsorber (25) by pressure compensation at outlet (6). The cells are eluted with buffers in a pH range of 2–3, and the suspension is transferred into a reaction chamber (26), where the cells are lysed. The entire lysate is transferred into a module (27) which contain a glass fleece. The nucleic acids are then adsorbed to this fleece while all other sample components remain in the filtrate and are discarded together with the waste. After desorption with a buffer with a low ionic strength, the nucleic acid-containing liquid is transferred into an amplification chamber (14).

In the device described above, the transport of liquid is implemented by means of one single multi-path valve (28), by applying a low pressure, and by means of aeration (6).

Figure 5:
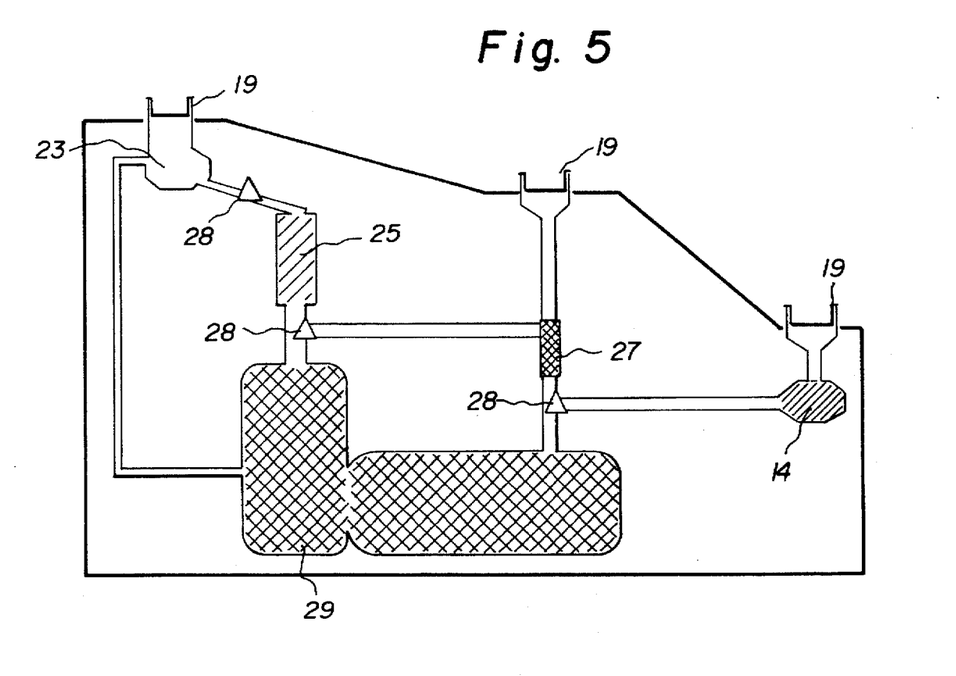

FIG. 5 shows a single-unit device for the treatment of EDTA blood. The liquid is transported via a waste fleece (29) (capillary forces combined with gravitational forces). Preincubation, e.g. enzymatic liquefaction and the above-mentioned hemolysis, occur in a first container (23). This is followed by an immunoadsorber (25). The nucleic acids are then immobilized via a subsequent glass fleece (27) and separated from other sample components. Subsequently, the nucleic acid-containing solution is transferred into an amplification chamber (14). In the present case, the distribution elements (28) are three-way cocks.

Figure 6:
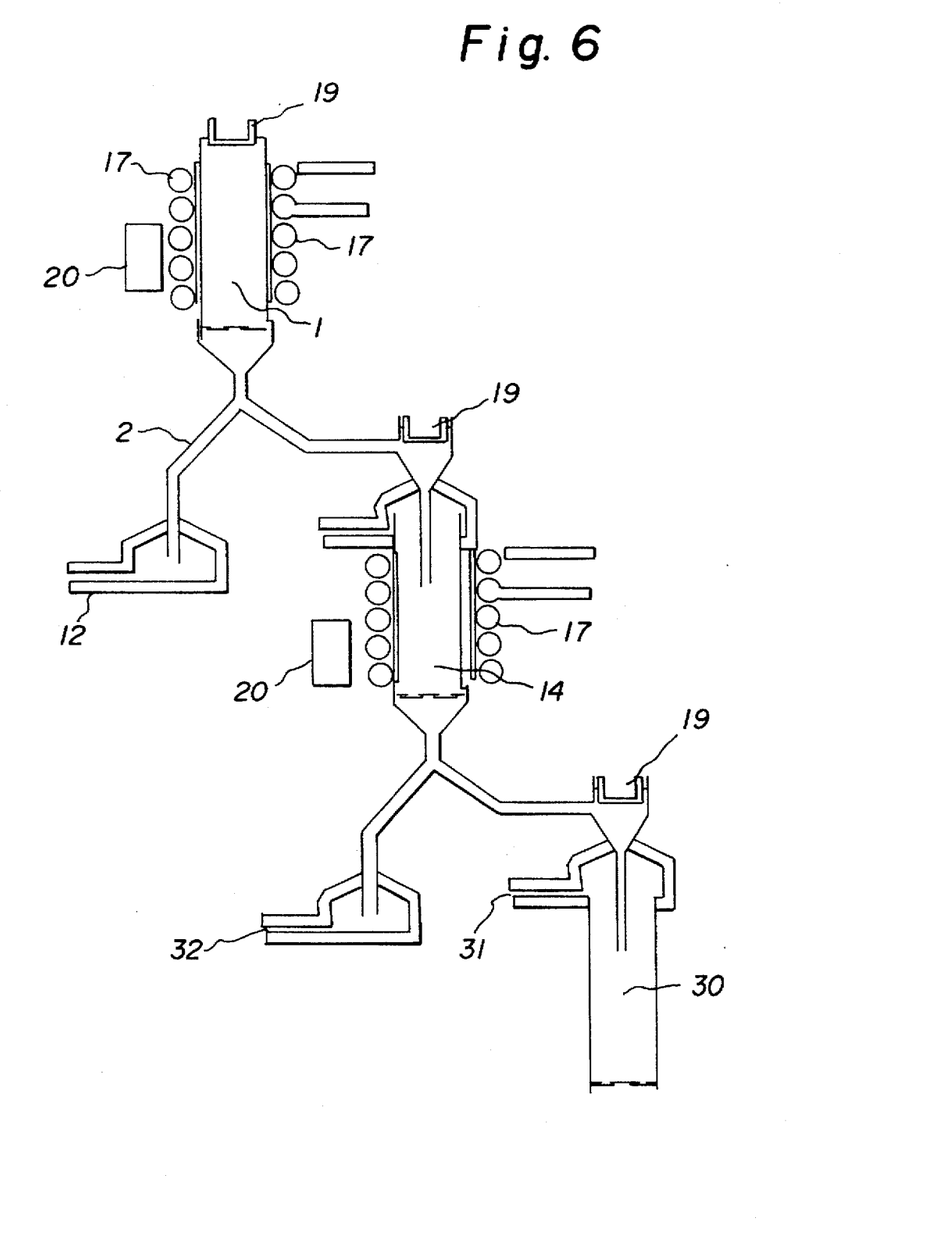

FIG. 6 is a schematic representation for the treatment of HIV-containing whole blood for the detection of DNA or RNA. For details, we refer to the description of FIG. 1 c. In addition, a magnet (20) is also provided in the first module. Moreover, the figure indicates that the amplified nucleic acids are transferred into a conventional tube (30) where the detection is carried out. This figure is described in greater detail in example 1.

Another subject matter of the invention is a system for the treatment of nucleic acids containing a device for pipetting liquids, a device for receiving a device according to claim 1 and a device for the controlled transport of gases or liquids in the device according to claim 1. The devices used for pipetting liquids can be conventional pipetting instruments as manufactured by Tecan. With these instruments, it is possible to transfer both the nucleic acid-containing sample liquid and all possibly necessary reagents from the sample and reagent storage containers into the device of the invention. In the device of the invention, transportation is preferably controlled by applying a low pressure. To accomplish this, a connecting opening of the device is linked to an element able to generate a low pressure. Controlling the distribution elements and/or the low pressure system ensures that transportation of the liquid from the individual reaction chambers is continued as desired.

Another subject matter of the invention is a method of separating and amplifying nucleic acids from a sample in the following steps:

Immobilizing nucleic acids in a first reaction chamber

Removing other sample components from the immobilized nucleic acids via a controlled path of transportation Immobilizing the nucleic acids and transferring the nucleic acid-containing liquids via controllable path of transportation to a second reaction chamber Amplification of the nucleic acids in a second reaction chamber.

Advantages of the invention include the highly flexible use of the modules, the possibility to minimize contamination, and the automation of sample preparation amplification in the analysis of nucleic acids. The modules are preferably designed as disposable elements. The most significant advantage of the invention is, however, to have eliminated centrifugation during sample preparation and amplification.

The following examples explain the invention in greater detail:

EXAMPLE 1a

Determination of HIV-DNA from whole blood
(FIG. 6)

Human antibodies (manufactured by Boehringer Mannheim Biochemicals, Cat. No.: 881 171) and streptavidin-magnetic particles (manufactured by Dynal, Oslo, Norway) and the HIV-DNA-containing cells from whole blood are suspended in the reaction module (1) with the aid of biotinylated anti-T-helper cells/CD4, then incubated and retained via a first magnet (20). By applying a vacuum to the waste container (16) via element (18), the excess whole blood can be washed out and removed.

When proteinase K is added in a suitable buffer system, e.g. with 1% Laureth 12 or 0.5% Tween 20 according to Rolfs et al. (in PCR: Clinical Diagnostics and Research, published by Springer Verlag, 1992) p. 84 et seq. or by using sodium dodecylsulfate according to Anderson and Diagnostic Molecular Biology—Principals and Applications, edited by D. H. Persing, T. F. Smith, F. C. Tenover, and T. J. White; American Society of Microbiology, ISBN 1-55581-056-X (1993), p. 197–202, the cells are first resuspended and lysed via thermal treatment in the first heater (17). After retention of the magnetic particles via magnet (20) and applying a vacuum to (18), the reaction mixture can be transferred to reaction module (14).

Subsequently, the PCR reagents are added via the automatically opening lid (19) and the DNA can be amplified according to EP-A-324474 by means of thermocycling via heater (17) of module (14). Then, hybridization is carried out by adding biotinylated DNA capture probe which is complementary to the PCR amplificate between the primer hybridization positions and heating via heater (17) of module (14). Subsequently, a vacuum is applied to (31) and the entire reaction mixture is subject to a detection reaction in a streptavidin(SA)-coated (ES) tube (30, manufactured by Boehringer Mannheim GmbH, Cat. No. 1602845) using an ES analyzer (manufactured by Boehringer Mannheim GmbH, Cat. No. 1602845) and the result is evaluated.

EXAMPLE 1b

This variant proposes a two-step process where the PCR reagent is replaced by silica gel with GuSCN buffer according to EP-A-0 389 063 which non-specifically absorbs the DNA. Excess material is removed by applying a vacuum to (32) provided a corresponding filter layer has been inserted into (14) prior to beginning the process. The nucleic acids are eluted from the silica gel with the aid of low salt buffer (10 mM Tris-hydrochloride-1 mM EDTA (pH 8.0) according to Boom et al., Journal of Clinical Microbiology, Vol. 28, No. 3, 1990; p. 496), followed by a PCR and in another intermediate module, hybridization and detection (as in 1a).

EXAMPLE 2

Determination of HIV-RNA from whole blood
(FIG. 6)

In (1), whole blood is subject to a hemolysis according to Rolfs et al. (in PCR: Clinical Diagnostics and Research, Springer Verlag, 1992). Subsequently, virus particles are separated via SA-coated magnetic beads (manufacturer: as in example 1) by adding biotinylated anti-gp 120 antibodies (sheep) (manufactured by Aalto Bio Reagents Ltd., Dublin, Ireland). They are then processed according to example 1a or 1b, where the PCR for the amplification of RNA is replaced by an RT-PCR corresponding to Wilber et al. in Diagnostic Molecular Microbiology—Principals and Applications, edited by D. H. Persing, T. F. Smith, F. C. Tenover and T. J. White; American Society of Microbiology; ISBN 1-55581-056-X (1993), p. 327–331.

EXAMPLE 3

Processing tissue

Tissue is transferred into individual cells corresponding to the pronase-EDTA method or the collagenase-pronase- EDTA method according to Lewin et al. in "Methods in Enzymology" vol. 171 "Biomembranes", edited by S. Fleischer and B. Fleischer, Academic Press, p. 444 et seq., by heat treatment with the aid of heater (17) to 37° C. in reaction module (1). Specific cells which are added to the PCR according to example 1a or 1b are isolated and purified with the aid of specific biotinylated cell surface markers corresponding to Garcia-Perez et al. in "Methods in Enzymology", vol. 171 "Biomembranes", edited by S. Fleischer and B. Fleischer, Academic Press, p. 581, and with the aid of magnetic particles (manufacturer as in example 1).

EXAMPLE 4

Digestion of sputum for the diagnosis of mycobacteria

For liquefaction according to the method described by Rolfs et al. (in PCR: Clinical Diagnostics and Research, published by Springer Verlag, 1992) p. 74 et seq., sputum is added into reaction module (1) together with N-acetyl-L-cystein/NaOH solution. The reaction can be accelerated by slightly heating it up with the aid of heating element (17). The centrifugation steps mentioned in the original literature reference are replaced by the use of specific biotinylated antibodies to surface markers of mycobacteria manufactured according to Garcia-Perez et al. in "Methods in Enzymology" vol. 171 "Biomembranes", edited by S. Fleischer and B. Fleischer, Academic Press, p. 581, and by using streptavidin-coated magnetic particles (manufacturer as in example 1). Specific cells are then isolated and treated as in example 3.

EXAMPLE 5

Column chromatography for cell isolation in the detection of HIV-DNA

Prior to adding the HIV-containing sample, reaction module (1) is filled with streptavidin-coupled bromocyane-activated sepharose (streptavidin manufactured by Boehringer Mannheim 1097679; the method is described in "Immunchemische Charakterisierung derATP-Synthetase von E. coli K2", G. Bienhaus, Dissertation, University of Tubingen, p. 66, 1980). Reagents are then added according to example 1a. After the reaction is completed, excess material is separated by applying a vacuum to (4) provided a corresponding filter layer has been inserted in (1).

EXAMPLE 6

Use of NASBA instead of PCR

Instead of a PCR, it is also possible to use an NASBA method (Cangene U.S. Pat. No. 5,130,239) where a constant temperature is generated via heater (17) of module (14).

EXAMPLE 7

Ion-exchange chromatography instead of glass fleece

Instead of variant 1b it is also possible to use an ion-exchange chromatography for isolating the nucleic acids according to DE 41 39 664.

List of reference numerals

1 Universal module
2 Bottom of 1
3 Outlet openings in 2

-continued

List of reference numerals

4 Rubber sealing lip
5 Slit in 4
6 Bore for aeration in 1
7 Paper fleece disk
8 Slit rubber sealing lip
9 Distribution element
10 Projection
11 First reaction chamber
12 Projection for waste container
13 Projection for second module
14 Reaction chamber
15 Opening
16 Waste container
17 Heating elements
18 Connecting element for vacuum
19 Lid
20 Magnet
21 Distribution element
22 Capillaries
23 Reaction module
24 Coarse filter
25 Immunoadsorber
26 Reaction chamber
27 Module
28 Multi-path valve
29 Waste fleece
30 Tube
31 Connecting element for vacuum
32 Connecting element for vacuum

We claim:

1. A device for treating nucleic acids in a sample solution, said device comprising:
   a first reaction chamber for separating nucleic acids from other sample components in the sample solution;
   a second reaction chamber for the amplification of purified nucleic acids which have been conveyed to the second reaction chamber by means of a transport path.
   a transport path connecting said first reaction chamber to the second reaction chamber;
   a controlling means connected to the transport path for controlling liquid flow through the transport path into the second reaction chamber wherein said controlling means allows nucleic acids separated from other sample components in the sample solution to be transported into the second reaction chamber and prevents liquid containing said other sample components from being transported into the second reaction chamber thereby conveying purified nucleic acids to said second reaction chamber.

2. A device according to claim 1, wherein said first reaction chamber, said second reaction chamber, and said transport path are configured to be a closed system during a treatment of nucleic acids therein, said closed system including at least one selectively openable opening in one of said first reaction chamber nd said second reaction chamber, for adding reagents thereto.

3. A device according to claim 1, wherein said second reaction chamber includes an opening for removing a reaction mixture therefrom.

4. A device as recited in claim 1, wherein said first reaction chamber includes immobilization means for immobilizing nucleic acids therein.

5. A device according to claim 1, wherein said transport path comprises three-way distribution means for distributing substances along three paths therein, the first path leading from said three-way distribution means to the first reaction chamber, the second path leading from the three-way distribution means to the second reaction chamber, and the third path leading from the three-way distribution means to a waste chamber.

6. A device as recited in claim 1, further comprising heating means for heating at least one of the first and second reaction chambers.

7. A device as recited in claim 1, wherein said second reaction chamber comprises an opening therein for the addition of reagents, said reagents being used for an amplification reaction, said second reaction chamber also having closing means for selectively closing said opening.

8. A device as recited in claim 2, wherein at least said first reaction chamber and said second reaction chamber comprise removable and replaceable elements.

9. A device according to claim 1, wherein said first reaction chamber and said second reaction chamber are of a modular design and can be assembled and disassembled, such that a plurality of first reaction chambers and second reaction chambers can be modularly configured to provide an apparatus which can be used as a multi-step reaction apparatus.

10. A device according to claim 1, wherein at least one of said first reaction chamber and said second reaction chamber can be emptied by the application of a vacuum thereto.

11. A device as recited in claim 1, wherein atleast one of said first reaction chamber and said second reaction chamber includes magnetic separation means for magnetically separating magnetic phases from non-magnetic phases of said sample.

12. A device as recited in claim 4, wherein said apparatus includes a plurality of first reaction chambers and second reaction chambers, for a multiplicity of applications.

13. A system for the treatment of nucleic acids obtained from a sample solution said system comprising:
    pipetting means for pipetting liquids therethrough;
    receiving means coupled to said pipetting means for receiving a plurality of the devices of claim 1.

14. A system as recited in claim 13, further comprising heating means for heating at least one of said plurality of devices.

15. A system as recited in claim 13, further comprising at least one magnet positioned adjacent to at least one of said plurality of devices.

16. A module for treatment of nucleic acid containing fluids, said module comprising:
    A treatment chamber for separating nucleic acids from other sample components in a sample;
    a closure coupled to said treatment chamber which is configured to be open and closed from the outside of said chamber by applying a vacuum to said closure, said closure enclosing and sealing said treatment chamber when closed.

17. A module as recited in claim 16, wherein said closure comprises a valve, and said valve is mounted to a bottom of said treatment chamber.

18. A method for treating nucleic acids in a sample, said method comprising:
    providing a device according to claim 1 and placing the sample solution into the first reaction chamber of said device wherein nucleic acids in said sample solution are concentrated and separated from other sample components in the sample solution thereby concentrating and purifying said nucleic acids;
    transporting said concentrated and purified nucleic acids to the second reaction chamber through the transport path by operating said controlling means; and
    amplifying said purified nucleic acids which have been conveyed to the second reaction chamber by means of the transport path.

19. A device for treating nucleic acids in a sample solution, said device comprising:
    a first reaction means for separating nucleic acids from other sample components in the sample solution;
    a second reaction means for the amplification of purified nucleic acids which have been conveyed to the second reaction chamber by means of a transport path;
    a transport path connecting said first reaction means to the second reaction means;
    a controlling means connected to the transport path for controlling liquid flow through the transport path into the second reaction means wherein said controlling means allows nucleic acids separated from other sample components in the sample solution to be transported into the second reaction means and prevents liquid containing said other sample components from being transported into the second reaction means thereby conveying purified nucleic acids to said second reaction means.

20. A device according to claim 19, further comprising at least one selective sealing means for selectively sealing a system formed by the first reaction means, the second reaction means, and the transport means.

21. A device according to claim 1, wherein said controlling means comprises a valve.

22. A device according to claim 1, wherein said controlling means also controls an enrichment of nucleic acids by controlling an amount of nucleic acid containing solution flowing into the second reaction chamber.

23. A device according to claim 1, wherein said controlling means also controls the amplification of the nucleic acids by controlling an amount of nucleic acid containing solution flowing into the second reaction chamber.

24. A device according to claim 21, wherein said valve opens when a vacuum pressure is applied to the first reaction chamber.

25. A system according to claim 13, further comprising a controlling means coupled to said transport means for said controlled transport of fluid.

26. A device according to claim 23, wherein said controlling means controls an amplification of nucleic acids in at least one reaction chamber of the plurality of reaction chambers.

27. A device according to claim 26, wherein said controlling means also controls an enrichment of the sample being transported through the transport means by controlling an amount of nucleic acid containing solution flowing into the second reaction chamber.

28. A system according to claim 25, wherein said control means comprises a valve.

29. A device according to claim 19, further comprising controlling means coupled to said transport means, for controlling the sample being transported through the transport means.

30. A device according to claim 29, wherein said control means comprises a valve.

31. A method according to claim 18, wherein said providing step includes a substep of providing a controlling means for controlling a concentration of nucleic acids in the sample.

32. A module as recited in claim 16, wherein said closure controls a treatment of the sample in the treatment chamber.

33. A method for treating nucleic acids in a sample, said method comprising:
    providing a device according to claim 1;
    placing a sample containing nucleic acids into the first reaction chamber of said device wherein said sample is liquefied in the first reaction chamber;

transporting said liquefied sample to the second reaction chamber of the device through the transport path by operating the controlling means; and combining said nucleic acids of said liquefied sample with nucleic acid amplifying reagents which have been placed in the second reaction chamber; and amplifying said nucleic acids.

34. A method as recited in claim 33, wherein said separation step comprises retaining said nucleic acids from said sample in a filer material.

35. A method as recited in claim 33, wherein said separation step comprises non-specific immobilization of said nucleic acids to an adsorbent contained in said first reaction chamber.

36. A method as recited in claim 33, wherein said separation step comprises biospecific immobilization of said nucleic acids to biospecific adsorbents.

37. A method as recited in claim 33, wherein said step of liquefying said sample includes a step of separating nucleic acids from substance interfering with a subsequent samplification of said nucleic acids, thereby producing the prepared sample.

38. A method for treating nucleic acids in a sample, said method comprising:

providing a device according to claim 1;

placing a sample containing nucleic acids into the first reaction chamber of said device wherein nucleic acids are separated from substances in the solution that inhibit nucleic acid amplification;

transporting said separated nucleic acids in the sample solution to the second reaction chamber of the device through the transport path by operating the controlling means; and combining said separated nucleic acids with nucleic acid amplifying reagents which have been placed in the second reaction chamber; and amplifying said purified nucleic acids.

39. A method as recited in claim 38, wherein said step of separating nucleic acids includes liquefying the sample, thereby producing the prepared sample.

40. A method as recited in claim 38, wherein said separation step comprises retaining said nucleic acids from said sample in a filter material.

41. A method as recited in claim 39, wherein said separation step comprises nonspecific immobilization of said nucleic acids to an adsorbent contained in said first reaction chamber.

42. A method as recited in claim 38, wherein said separation step comprises biospecific immobilization of said nucleic acids to biospecific adsorbents.

* * * * *